(12) United States Patent
Burkholz et al.

(10) Patent No.: US 11,969,247 B2
(45) Date of Patent: Apr. 30, 2024

(54) EXTENSION HOUSING A PROBE OR INTRAVENOUS CATHETER

(71) Applicant: Becton, Dickinson and Company, Franklin Lakes, NJ (US)

(72) Inventors: Jonathan Karl Burkholz, Salt Lake City, UT (US); Bryan Bihlmaier, Provo, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 408 days.

(21) Appl. No.: 16/037,246

(22) Filed: Jul. 17, 2018

(65) Prior Publication Data

US 2019/0021640 A1 Jan. 24, 2019

Related U.S. Application Data

(60) Provisional application No. 62/534,552, filed on Jul. 19, 2017.

(51) Int. Cl.
*A61B 5/15* (2006.01)
*A61B 5/153* (2006.01)
(Continued)

(52) U.S. Cl.
CPC .... *A61B 5/150992* (2013.01); *A61B 5/15003* (2013.01); *A61B 5/150343* (2013.01);
(Continued)

(58) Field of Classification Search
None
See application file for complete search history.

(56) References Cited

U.S. PATENT DOCUMENTS 2,893,395 A * 7/1959 Buck ............ A61M 39/00
604/533
3,185,152 A * 5/1965 Ring ............ A61M 25/0111
604/159

(Continued)

FOREIGN PATENT DOCUMENTS

CN 103906470 7/2014
EP 2272432 1/2011

(Continued)

OTHER PUBLICATIONS

"BD Q-SYTE Luer Access Split Septum", BD Medical, 2007, 4 pages (Year: 2007).*

(Continued)

*Primary Examiner* — Matthew Kremer
(74) *Attorney, Agent, or Firm* — The Webb Law Firm

(57) ABSTRACT

A vascular access device may include a housing, which may include a proximal end, a distal end, and a slot. The distal end of the housing may be configured to be coupled to a catheter assembly. The vascular access device may also include an instrument disposed within the housing. The instrument may include a catheter or a probe. The instrument may include a proximal end and a distal tip. The proximal end of the instrument may extend through the slot and may be configured to move along the slot to move the instrument from a proximal position to a distal position. In response to movement of the proximal end of the instrument from the proximal position to the distal position, the catheter may be advanced beyond the distal end of the housing into the catheter assembly and/or vasculature of a patient.

18 Claims, 7 Drawing Sheets

(51) Int. Cl.
| | |
|---|---|
| *A61M 25/01* | (2006.01) |
| *A61M 39/12* | (2006.01) |
| *A61M 5/31* | (2006.01) |
| *A61M 25/00* | (2006.01) |
| *A61M 25/06* | (2006.01) |
| *A61M 39/10* | (2006.01) |
| *A61M 39/16* | (2006.01) |

(52) U.S. Cl.
 CPC .. *A61B 5/150389* (2013.01); *A61B 5/150633* (2013.01); *A61B 5/153* (2013.01); *A61M 25/0113* (2013.01); *A61M 39/12* (2013.01); *A61B 5/150732* (2013.01); *A61M 5/31* (2013.01); *A61M 25/0097* (2013.01); *A61M 25/0111* (2013.01); *A61M 25/0693* (2013.01); *A61M 2039/1066* (2013.01); *A61M 2039/1072* (2013.01); *A61M 2039/1077* (2013.01); *A61M 39/162* (2013.01)

(56) References Cited

U.S. PATENT DOCUMENTS

| | | | |
|---|---|---|---|
| 3,262,448 A | | 7/1966 | Ring et al. |
| 3,572,333 A | * | 3/1971 | Hubert ................ B29C 66/8322 604/170.01 |
| 3,739,778 A | * | 6/1973 | Monestere, Jr. ... A61M 25/0111 604/167.01 |
| 4,068,659 A | | 1/1978 | Moorehead |
| 4,079,738 A | | 3/1978 | Dunn et al. |
| 4,297,316 A | * | 10/1981 | Cunningham ........ A61M 39/12 422/38 |
| 4,417,886 A | | 11/1983 | Frankhouser et al. |
| 4,730,624 A | * | 3/1988 | Waters ............... A61B 5/15003 604/220 |
| 4,795,434 A | * | 1/1989 | Kujawski ............. A61B 5/1459 600/585 |
| 5,100,394 A | * | 3/1992 | Dudar .................. A61M 39/14 604/537 |
| 5,148,811 A | * | 9/1992 | Messinger ........... A61B 5/0215 600/486 |
| 6,524,299 B1 | | 2/2003 | Tran et al. |
| 6,719,772 B2 | * | 4/2004 | Trask ................ A61M 39/0613 606/191 |
| 2004/0073171 A1 | * | 4/2004 | Rogers .................. A61M 39/26 604/164.13 |
| 2007/0088279 A1 | * | 4/2007 | Shue ................ A61M 25/0693 604/168.01 |
| 2007/0088295 A1 | | 4/2007 | Bankiewicz |
| 2007/0179474 A1 | * | 8/2007 | Cahill .................... A61M 39/02 604/533 |
| 2010/0210934 A1 | | 8/2010 | Belson |
| 2011/0306953 A1 | * | 12/2011 | Pineau .................. A61M 25/01 606/1 |
| 2012/0016307 A1 | | 1/2012 | Burkholz et al. |
| 2012/0197200 A1 | | 8/2012 | Belson |
| 2013/0237925 A1 | * | 9/2013 | Trainer ............. A61M 39/0693 604/247 |
| 2014/0046214 A1 | * | 2/2014 | Devgon ............ A61B 5/15003 600/581 |
| 2014/0343456 A1 | * | 11/2014 | Cabot .............. A61B 5/150236 600/581 |
| 2014/0364766 A1 | * | 12/2014 | Devgon ............ A61B 5/15003 600/581 |
| 2016/0045715 A1 | * | 2/2016 | Galgano ........... A61M 25/0662 604/510 |
| 2017/0120001 A1 | | 5/2017 | Hyer et al. |
| 2019/0021640 A1 | | 1/2019 | Burkholz et al. |

FOREIGN PATENT DOCUMENTS

| | | |
|---|---|---|
| EP | 2569046 | 3/2013 |
| GB | 1066751 | 4/1967 |
| JP | 2006-513809 | 4/2006 |
| JP | 2010-505548 | 2/2010 |
| JP | 7231609 B2 | 3/2023 |
| WO | 98/39054 | 9/1998 |
| WO | 2019018473 A3 | 1/2019 |

OTHER PUBLICATIONS

BE Nexiva Closed IV Catheter System, BD Medical, 2009, 15 pages (Year: 2009).*
Velano Vascular, "Introducing PIVO", http://velanovascular.com/solutions/, 2017.

* cited by examiner

EXTENSION HOUSING A PROBE OR INTRAVENOUS CATHETER

CROSS-REFERENCE TO RELATED APPLICATIONS

This application claims the benefit of U.S. Provisional Patent Application No. 62/534,552 filed Jul. 19, 2017, entitled EXTENSION HOUSING A PROBE OR INTRAVENOUS CATHETER, which is incorporated herein in its entirety.

BACKGROUND OF THE INVENTION

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is required, an additional needle stick is needed to provide vein access for blood collection, which may be painful for the patient and result in higher material costs. Accordingly, there is a need for catheter systems and methods that facilitate placement of blood sample instruments, such as, for example, catheters, and probe instruments in the vasculature of the patient without additional needle sticks.

BRIEF SUMMARY OF THE INVENTION

The present application relates generally to an extension or introducer that may house an instrument, such as, for example, a probe or an intravenous catheter, as well as related systems and methods. In some embodiments, the extension may include a vascular access device that allows the instrument to access vasculature of a patient through another vascular access device, such as, for example, a catheter assembly, which may be inserted into the vasculature of the patient. In some embodiments, when the instrument is introduced into the catheter assembly via the extension, the instrument may access a fluid pathway of the catheter assembly and/or the instrument may extend through the catheter assembly and access the vasculature of the patient.

In some embodiments, the extension may include a blood collection device, which may be used to obtain a blood sample. In some embodiments, a catheter of the catheter assembly with significant indwelling time may be susceptible to narrowing, collapse, kinking, blockage by debris (e.g., fibrin or platelet clots), and adhering of a tip of the catheter to the vasculature. Thus, blood withdrawal using the catheter may be difficult. In some embodiments, the instrument may include another catheter that may be disposed within the extension, and the other catheter may provide access to the vasculature of the patient without any additional needle sticks. Thus, in some embodiments, the extension may be used for needle-free blood collection and/or fluid infusion. Advantageously, in some embodiments, the extension may also allow maintenance of a closed system and aseptic technique, while reducing disturbance or dislodgement of the catheter and/or catheter securement dressing.

In some embodiments, the instrument may include a probe, which may be disposed within the extension. In some embodiments, the probe may include one or more openings and/or one or more sensors. In some embodiments, the openings and/or the sensors may be disposed towards a distal tip of the probe. In some embodiments, the openings may serve as fluid inlets and/or outlets. In some embodiments, the sensors may measure one or more parameters and/or detect one or more elements related to, for example, diagnostic information, blood chemistry, pressure, flow rate, drug identification, microbes, placement of an implantable stent, in-vein catheter tip stabilization feature, or other device, etc. In some embodiments, the extension may facilitate placement of a portion of the probe that includes the sensors within the fluid pathway of the catheter assembly and/or the vasculature of the patient. In some embodiments, the instrument may function as both the probe and the other catheter, including elements of both the probe and the other catheter.

In some embodiments, the catheter assembly may include one or more of the following: the catheter, a catheter adapter, a septum housing, and a septum. In some embodiments, the catheter may be secured within and extend distally from the catheter adapter. In some embodiments, the catheter assembly may include a peripheral IV catheter assembly. In some embodiments, the catheter adapter may include a distal end, a proximal end, and a lumen extending therebetween. In some embodiments, the septum may be disposed within the lumen of the catheter adapter. In some embodiments, the septum may be at least partially disposed within the septum housing and configured to at least substantially seal the lumen of the catheter adapter. In some embodiments, the septum housing may prevent dislodgement or destabilization of the septum, thereby preventing leakage of fluid from the lumen of the catheter adapter.

In some embodiments, the extension may be coupled with a closed IV catheter assembly or a catheter assembly with an integrated extension tube, such as, for example, the Becton Dickinson NEXIVA™ Closed IV Catheter System or the Becton Dickinson NEXIVA™ DIFFUSICS™ Closed IV Catheter System. In these and other embodiments, a proximal end of the catheter adapter may include a first port and a second port. In these and other embodiments, the lumen of the catheter adapter may include a first lumen and/or a second lumen. In some embodiments, the first port may form the first lumen and/or the second port may form the second lumen. In some embodiments, the first and second lumens may join at a common lumen. In some embodiments, the first lumen may be generally aligned with the common lumen and/or the second port may include a side port. In some embodiments, the septum and/or the septum housing may be disposed in the first lumen.

In some embodiments, the second lumen of the catheter adapter may be coupled with the extension via an extension tube that may extend from the second port of the catheter adapter, as will be explained later in further detail. In some embodiments, an introducer needle of the catheter assembly may be withdrawn through the catheter adapter after insertion of the catheter into the vasculature of the patient. In the closed IV catheter system, when the introducer needle is withdrawn through the catheter adapter, the first lumen, which may correspond to a "needle channel," may be closed off by the septum from an external environment surrounding the catheter adapter. Thus, the septum may at least substantially seal the first port and prevent fluid from exiting the catheter adapter through the first port. In some embodiments, a fluid pathway of the catheter assembly during fluid infusion and/or blood withdrawal may extend through the second port and not the first port. In some embodiments, the septum and/or the septum housing may be disposed proximal to the second port of the catheter adapter.

In some embodiments, the catheter assembly may include another type of catheter assembly, such as, for example, a non-integrated catheter assembly or a catheter assembly without the integrated extension tube. In some embodiments, the extension may be coupled to the non-integrated catheter assembly.

In some embodiments, the extension may include a barrel or housing, which may include a proximal end and a distal end. In some embodiments, the distal end of the housing may include a coupling mechanism, which may couple the extension with the catheter assembly. In some embodiments, the coupling mechanism may be coupled directly to the catheter adapter. In some embodiments, a proximal end of the extension tubing of the catheter assembly may be coupled with an adapter or coupler element, which may be coupled to the extension. In some embodiments, the coupler element may include a y-adapter, a single port, or dual ports. In some embodiments, the coupler element may include a luer fitting and/or a blood control valve. In some embodiments, the coupler element may include a luer fitting and a removable or non-removable needle-free connector.

In some embodiments, the instrument may be at least partially disposed or housed within the housing. In some embodiments, the housing may at least partially surround the instrument, which may protect the instrument from the external environment surrounding the extension. In some embodiments, the housing may include a slot, which may extend parallel to a longitudinal axis of the housing. In these and other embodiments, the housing may be rigid or semi-rigid.

In some embodiments, the extension may include an adapter, which may be coupled to a proximal end of the instrument. In some embodiments, the adapter may be configured to move along the slot from a proximal position to a distal position and/or from the distal position to the proximal position. In some embodiments, in response to movement of the adapter along the slot from the proximal position to the distal position, the instrument is advanced beyond the distal end of the housing. In some embodiments, in response to movement of the adapter along the slot from the distal position to the proximal position, the instrument may be withdrawn into the housing. In some embodiments, the distal end of the housing may include an elastomer or other suitable material seal to provide a fluid seal between the distal end of the extension housing and the instrument.

In some embodiments, the adapter may include a cavity configured to receive, for example, a syringe and/or blood collection tube. In some embodiments, the adapter may include a cannula disposed within the cavity and configured to puncture a septum of the syringe in response to the syringe being advanced into the cavity of the adapter. Additionally or alternatively, in some embodiments, the cannula may be configured to puncture a septum of the blood collection tube in response to the blood collection tube being advanced into the cavity of the adapter.

In some embodiments, the adapter may be coupled with the proximal end of the instrument in any number of ways. In some embodiments, the adapter may be integrally formed with the proximal end of the instrument. In some embodiments, the adapter may be permanently coupled with the proximal end of the instrument or monolithically formed as a single piece with the proximal end of the instrument. In some embodiments, the adapter may be selectively coupled with the proximal end of the instrument. For example, the proximal end of the instrument may include a luer fitting, which may be coupled with a corresponding luer fitting of the adapter. In some embodiments, the luer fitting of the proximal end of the instrument may correspond to a luer fitting of any number of devices. In some embodiments, the proximal end of the instrument may include or may be coupled with an instrumentation interface, an electrical connection, and/or an optical connection.

In some embodiments, the instrument may include the proximal end and a distal tip. In some embodiments, the proximal end of the instrument, which may include an instrument hub, may extend through the slot, which may allow the clinician to move the proximal end of the instrument along the slot to move the instrument from a proximal position to a distal position and/or from a distal position to a proximal position. In some embodiments, the proximal end of the instrument may include an instrument hub, as will be explained later in further detail. In some embodiments, the distal or draw position of the instrument and/or the adapter may correspond to a position for probing or collecting blood. In some embodiments, when the instrument is disposed in the proximal position, the proximal end of the instrument may be disposed at or near a proximal end of the slot. In some embodiments, when the instrument is disposed in the distal position, the proximal end of the instrument may be disposed at or near a distal end of the slot.

In some embodiments, the proximal end of the instrument may include a curved or angled portion, which may extend through the slot and/or may be coupled to the adapter or another device. In some embodiments, the adapter may be angled with respect to the housing. In some embodiments, the adapter may be oriented parallel to the longitudinal axis of the housing. In some embodiments, the extension may include an advancement tab, which may be coupled to the proximal end of the instrument and/or the adapter. In some embodiments, the clinician may pinch or grasp the advancement tab to move the instrument to the proximal position and/or the distal position. In some embodiments, the instrument is advanced beyond the distal end of the housing and/or the catheter when the adapter is disposed in the distal position. In some embodiments, the advancement tab may be offset from the slot, which may facilitate easy movement of the instrument and/or the adapter with respect to the slot. In some embodiments, the adapter may be used as the advancement tab.

In some embodiments, at least a portion of the housing may be axially-compressible or axially-collapsible. In some embodiments, the extension may include a sheath or sleeve. In some embodiments, the sleeve may at least partially surround the instrument. In these and other embodiments, the sleeve may shield the instrument from contaminants and/or isolate any blood or other fluids that may remain on the instrument after accessing the fluid pathway of the catheter assembly. In these and other embodiments, the sleeve may protect the instrument from the external environment surrounding the extension.

In some embodiments, the instrument may be at least partially disposed within the sleeve. In some embodiments, the sleeve may be axially-collapsible or axially-compressible. In further detail, in some embodiments, the instrument may be advanced to the distal position beyond a distal end of the sleeve when the sleeve is collapsed or compressed in the distal direction.

In some embodiments, a kit may include one or more of the following: the catheter assembly, the extension, the syringe, the blood collection tube, an alcohol swab, one or more disinfection caps, an antimicrobial skin preparation solution, and catheter securement dressing. In some embodiments, the dressing may include an extension tube slot and/or one or more antimicrobial agents. In some embodiments, the disinfection caps may include one or more antimicrobial agents and/or may be configured to close the coupler element and/or one or more catheter adapter ports. Specifically, in some embodiments, the kit may include a blood collection kit, and the instrument may include the other catheter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention. Moreover, the Figures may show simplified or partial views, and the dimensions of elements in the Figures may be exaggerated or otherwise not in proportion for clarity.

As used in the present disclosure, the terms "proximal" and "distal" may refer to the direction closer to and away from, respectively, a clinician who would place the catheter system into contact with a patient. Thus, for example, the end of the catheter system first touching the body of the patient would be the distal end, while the opposite end of the catheter system (e.g., the end of the device being manipulated by the clinician) would be the proximal end of the catheter system.

Figure 1A:
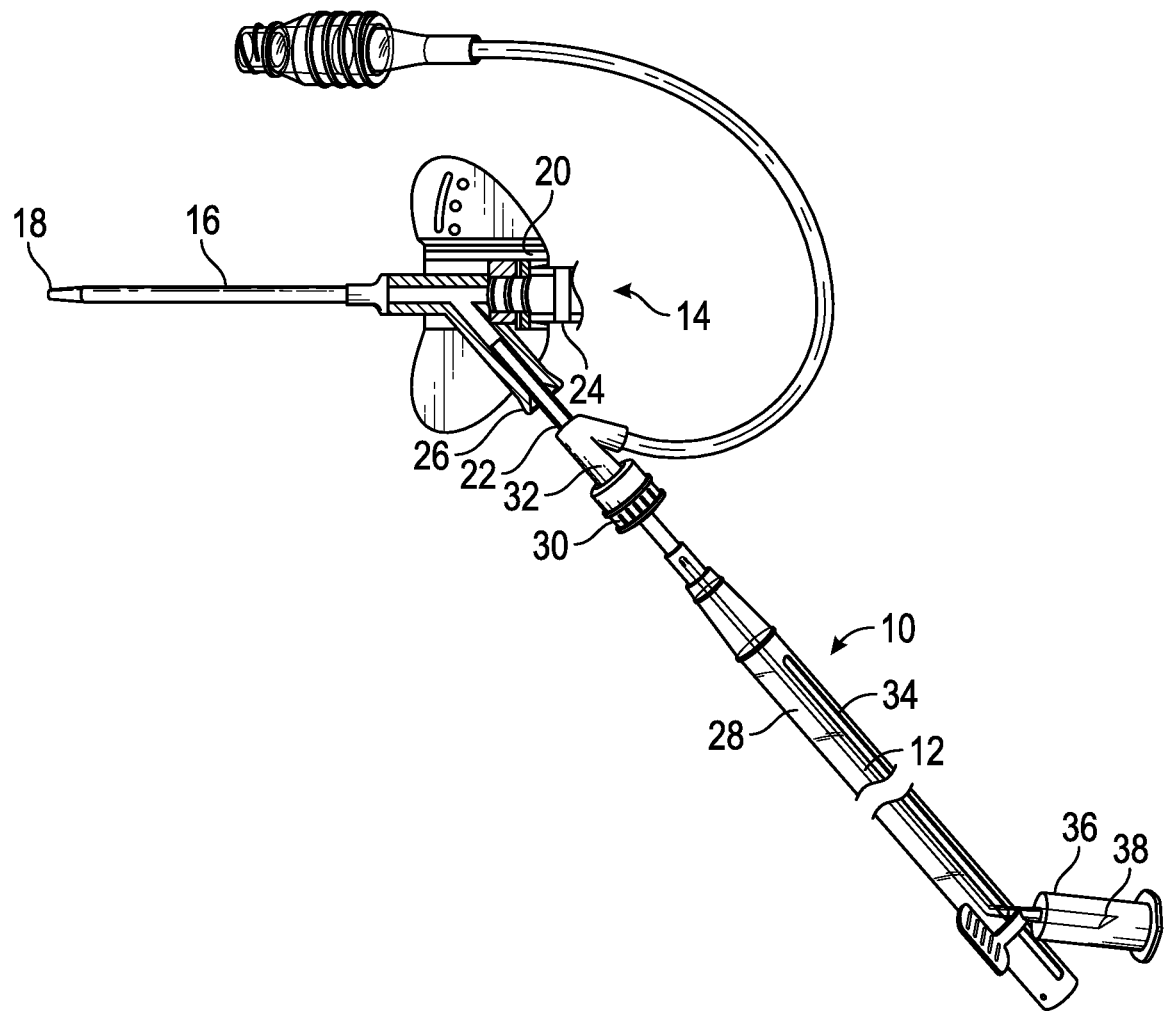
FIG. 1A is an upper perspective view of an example extension coupled with an example catheter assembly, illustrating an example instrument in a proximal position, according to some embodiments.
Figure 1B:
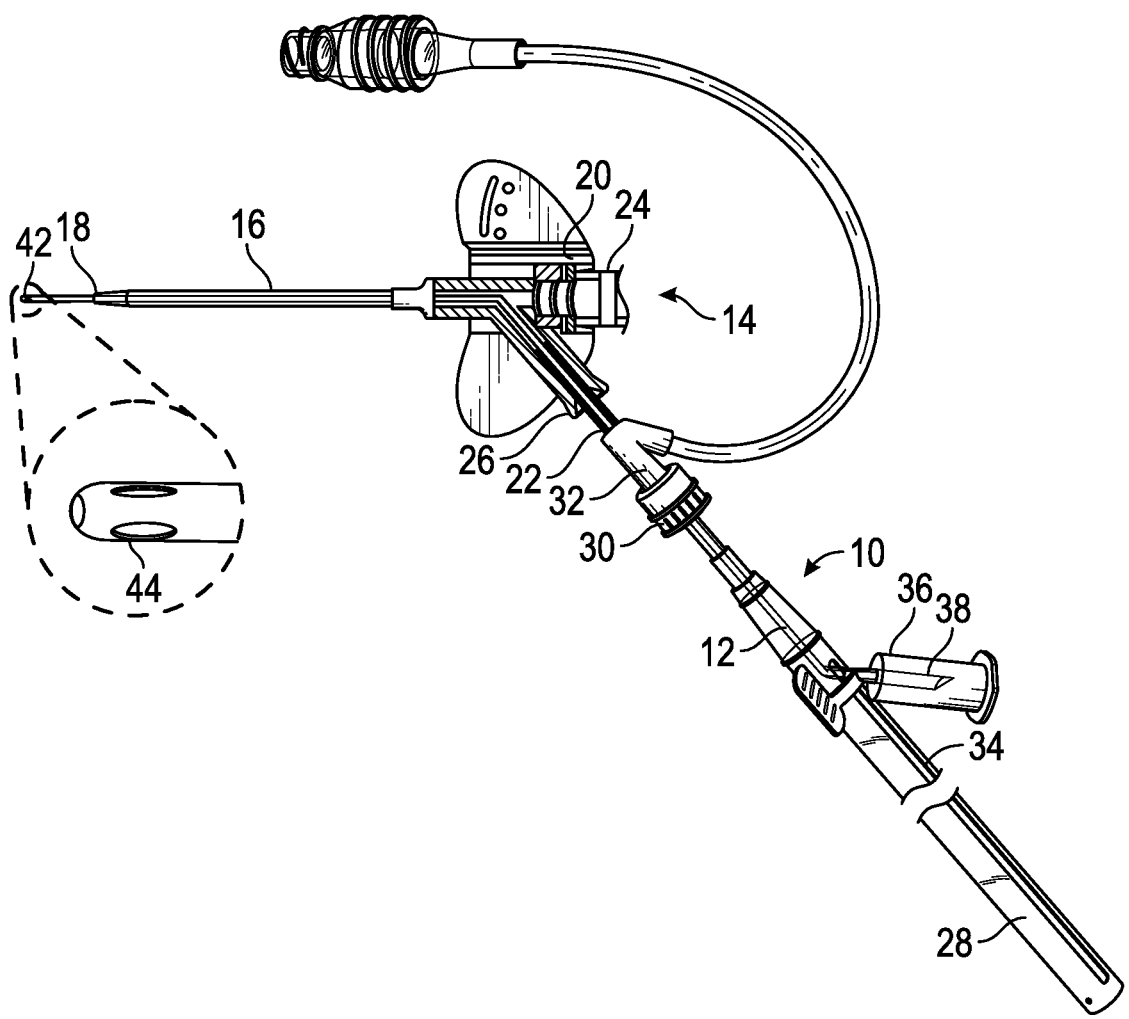
FIG. 1B is an upper perspective view of the extension of FIG. 1A coupled with the catheter assembly, illustrating the instrument in a distal position, according to some embodiments.

The present application relates generally to an extension that may house an instrument, such as, for example, a probe or an intravenous catheter, as well as related systems and methods. Referring now to FIGS. 1A-1B, in some embodiments, the extension 10 or introducer may be configured to introduce the instrument 12 into a catheter assembly 14. In some embodiments, when the instrument 12 is introduced into the catheter assembly 14, the instrument 12 may access a fluid pathway of the catheter assembly 14 and/or the instrument may extend through the catheter assembly 14 and access vasculature of a patient.

In some embodiments, the extension 10 may include a blood collection device, which may be used to obtain a blood sample. In some embodiments, a catheter 16 of the catheter assembly 14 with significant indwelling time may be susceptible to narrowing, collapse, kinking, blockage by debris (e.g., fibrin or platelet clots), and adhering of a tip 18 of the catheter 16 to the vasculature. Thus, blood withdrawal using the catheter 16 may be difficult. In some embodiments, the instrument 12 may include another catheter may be disposed within the extension, and the other catheter may provide access to the vasculature of the patient without any additional needle sticks without any additional needle sticks, as illustrated, for example, in FIG. 1B. Thus, in some embodiments, the extension 10 may be used for needle-free blood collection and/or fluid infusion.

In some embodiments, the instrument 12 may include a probe, which may be at least partially disposed within the extension 10. In some embodiments, the probe may include one or more openings and/or one or more sensors. In some embodiments, the openings and/or the sensors may be disposed towards a distal tip of the probe. In some embodiments, the openings may serve as fluid inlets and/or outlets. In some embodiments, the sensors may measure one or more parameters and/or detect one or more elements related to, for example, diagnostic information, blood chemistry, pressure, flow rate, drug identification, microbes, placement of an implantable stent, in-vein catheter tip stabilization feature, or other device, etc. In some embodiments, the extension 10 may facilitate placement of a portion of the probe that includes the sensors within the fluid pathway of the catheter assembly 14 and/or the vasculature of the patient. In some embodiments, the instrument 12 may function as both the probe and the other catheter, including elements of both the probe and the other catheter.

In some embodiments, the catheter assembly 14 may include one or more of the following: the catheter 16, a catheter adapter 20, a septum housing, and a septum. In some embodiments, the catheter 16 may be secured within and extend distally from the catheter adapter 20. In some embodiments, the catheter assembly 14 may include a peripheral IV catheter assembly. In some embodiments, the catheter adapter 20 may include a distal end, a proximal end, and a lumen extending therebetween. In some embodiments, the septum may be disposed within the lumen of the catheter adapter 20. In some embodiments, the septum may be at least partially disposed within the septum housing and configured to at least substantially seal the lumen of the catheter adapter. In some embodiments, the septum housing may prevent dislodgement or destabilization of the septum, thereby preventing leakage of fluid from the lumen of the catheter adapter.

In some embodiments, the extension 10 may be coupled with a closed IV catheter assembly or a catheter assembly with an integrated extension tube 22, such as, for example, the Becton Dickinson NEXIVA™ Closed IV Catheter System or the Becton Dickinson NEXIVA™ DIFFUSICS™ Closed IV Catheter System. In these and other embodiments, a proximal end of the catheter adapter 20 may include a first port 24 and a second port 26. In these and other embodiments, the lumen of the catheter adapter 20 may include a first lumen and/or a second lumen. In some embodiments, the first port 24 may form the first lumen and/or the second port 26 may form the second lumen. In some embodiments, the first and second lumens may join at a common lumen. In some embodiments, the first lumen may be generally aligned with the common lumen and/or the second port 26 may include a side port. In some embodiments, the septum and/or the septum housing may be disposed in the first lumen 24.

In some embodiments, the second lumen of the catheter adapter 20 may be coupled with the extension 10 via the extension tube 22 that may extend from the second port 26 of the catheter adapter 20, as will be explained later in further detail. In some embodiments, an introducer needle (not illustrated) of the catheter assembly 14 may be withdrawn through the catheter adapter 20 after insertion of the catheter 16 into the vasculature of the patient. In the closed IV catheter system, when the introducer needle is withdrawn through the catheter adapter 20, the first lumen 24, which may correspond to a "needle channel," may be closed off by the septum from an external environment surrounding the catheter adapter 20. Thus, the septum may at least substantially seal the first port 24 and prevent fluid from exiting the catheter adapter 20 through the first port 24. In some embodiments, a fluid pathway of the catheter assembly 14 during fluid infusion and/or blood withdrawal may extend through the second port 26 and not the first port 24. In some embodiments, the septum and/or the septum housing may be disposed proximal to the second port 26 of the catheter adapter 20.

In some embodiments, the catheter assembly 14 may include another type of catheter assembly, such as, for example, a non-integrated catheter assembly or a catheter assembly without the integrated extension tube 22. In some embodiments, the extension 10 may be coupled to the non-integrated catheter assembly. In some embodiments, the extension 10 may be coupled directly to a port of the non-integrated catheter assembly. In some embodiments, by accessing the fluid pathway and/or the vasculature through a particular septum and/or the first port 24, insertion of the instrument 12 through a longer path of the extension tube 22 or an integrated extension set may be avoided.

In some embodiments, the instrument 12 may be guided by one or more features, such as, for example, one or more tapered surfaces, to allow the instrument 12 to access a fluid pathway of the catheter assembly and/or the vasculature of the patient. Guidance of the instrument 12 through the catheter assembly 14 is described in further detail in U.S. Patent Application No. 62/534,557, filed Jul. 19, 2017, entitled "Systems and Methods to Improve Instrument Guidance Within an Intravenous Catheter Assembly," which is hereby incorporated by reference in its entirety.

In some embodiments, the extension 10 may include a barrel or housing 28, which may include a proximal end and a distal end. In some embodiments, the distal end of the housing 28 may include a coupling mechanism 30, which may couple the extension 10 with the catheter assembly 14. In some embodiments, the coupling mechanism 30 may be a luer fitting, such as, for example, a male luer fitting or a luer lock threaded collar. In some embodiments, the coupling mechanism 30 may include a non-luer coupling mechanism. In some embodiments, the coupling mechanism 30 may be part of an introducer element, as further described in further detail in U.S. Patent Application No. 62/534,557, filed Jul. 19, 2017, entitled "Systems and Methods to Improve Instrument Guidance Within an Intravenous Catheter Assembly."

In some embodiments, the coupling mechanism 30 may be coupled directly to the catheter adapter 20. In some embodiments, a proximal end of the extension tube 22 of the catheter assembly 14 may include an adapter or coupler element 32, which may be coupled to the corresponding coupling mechanism 30 of the extension 10. In some embodiments, the extension tube 22 may provide compliance and/or flexibility in the system, which may allow a length of the extension 10 to be shortened and/or prevent use of another extension tube, as will be explained later in further detail. In some embodiments, the coupler element 32 may include a y-adapter, a single port, or dual ports. In some embodiments, the coupler element 32 may include a luer fitting and/or a blood control valve. In some embodiments, the blood control valve may facilitate maintenance of the closed system and prevent blood leakage.

In some embodiments, the coupling mechanism 30 may include at least one valve, which may provide a fluid seal that is penetrated by the instrument. The valve of the coupling mechanism 30 may be disposed at any number of locations to prevent fluid from the catheter assembly 14 from entering all or a portion of one or more of the following: the coupling mechanism 30, a sleeve 55 (illustrated in FIGS. 2H-2I), and the housing 28. In some embodiments, the valve may include a septum and/or a slit. In some embodiments, the valve may cover a distal opening of the coupling mechanism 30. In some embodiments, the valve may be disposed within an inner lumen of the coupling mechanism 30 and/or extend across a diameter of the inner lumen.

In some embodiments, the instrument 12 may be at least partially disposed or housed within the housing 28. In some embodiments, the housing 28 may at least partially surround the instrument, which may protect the instrument 12 from the external environment surrounding the extension 10 and/or microbes. In some embodiments, the housing 28 may include a slot 34, which may extend parallel to a longitudinal axis of the housing 28. In these and other embodiments, the housing 28 may be rigid or semi-rigid. In some embodiments, the housing 28 may be clear or opaque.

In some embodiments, at least a portion of the housing 28 may be axially-compressible or axially-collapsible. For example, the housing 28 may include one or more collapsing and/or telescoping barrels. Additionally or alternatively, the housing 28 may include the slot 34. In some embodiments, a first concentric barrel may be advanced into a second concentric barrel. In some embodiments, at least a portion of the first concentric barrel and/or the second concentric barrel may be collapsible.

In some embodiments, the extension 10 may include an adapter 36, which may be coupled to a proximal end of the instrument 12. In some embodiments, the adapter 36 may be configured to move along the slot 34 from a proximal position to a distal position and/or from the distal position to the proximal position. In some embodiments, in response to movement of the adapter 36 along the slot 34 from the proximal position to the distal position, the instrument 12 is advanced beyond the distal end of the housing 28. In some embodiments, in response to movement of the adapter 36 along the slot 34 from the distal position to the proximal position, the instrument 12 may be withdrawn into the housing 28.

In some embodiments, the adapter 36 may include a cavity configured to receive, for example, a syringe and/or blood collection tube. In some embodiments, the adapter 36 may include a cannula 38 disposed within the cavity and configured to puncture a septum of the syringe in response to the syringe being advanced into the cavity of the adapter 36. Additionally or alternatively, in some embodiments, the cannula 38 may be configured to puncture a septum of the blood collection tube in response to the blood collection tube being advanced into the cavity of the adapter 36. In some embodiments, the adapter 36 may correspond to the Becton Dickinson VACUTAINER® one-use holder or a similar holder.

In some embodiments, the instrument 12 may include the proximal end and the distal tip 42. In some embodiments, the distal tip 42 may include one or more holes 44, which may be inlet and/or outlet holes. In some embodiments, the distal tip 42 may be constructed of a softer and/or less rigid material than the proximal end of the instrument 12 for buckling resistance. In some embodiments, the distal tip 42 may be blunt, straight, or tapered. In some embodiments, the proximal end of the instrument 12 may extend through the slot 34, which may allow the clinician to move the proximal end of the instrument 12 along the slot 34 to move the instrument from the proximal position to the distal position and/or from the distal position to the proximal position.

Figure 1C:
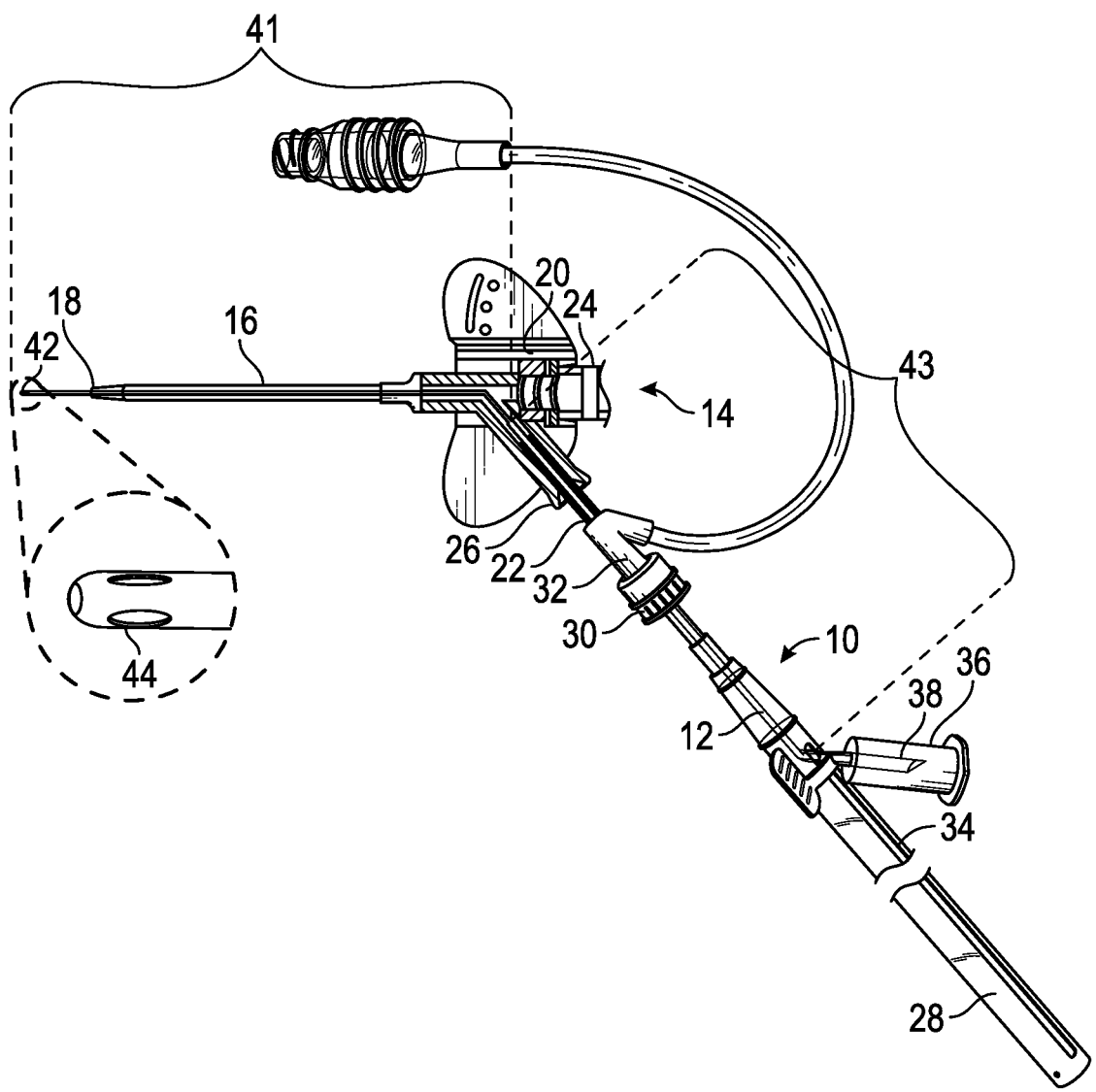
FIG. 1C is an upper perspective view of an example instrument having a variable outer diameter, according to some embodiments.

Referring now to FIG. 1C, in some embodiments, the instrument 12 may include a variable outer diameter. In some embodiments, a distal portion 41 of the instrument may have a smaller outer diameter than a proximal portion 43 of the instrument 12. Additionally or alternatively, the instrument 12 may have variable stiffness along a length of the instrument 12. In some embodiments, the distal portion 41 may be configured to bend at a transition from the second lumen of the catheter adapter 20 to the common lumen, as illustrated in FIG. 1C. In these and other embodiments, the proximal portion 43 may be more rigid than the distal portion 41. In some embodiments, the distal portion 41 may be more rigid than the proximal portion 43 or Referring now to FIGS. 2A-2F, in some embodiments, the adapter 36 may be coupled with the proximal end of the instrument 12 in any number of ways. In some embodiments, the adapter 36 may be removably or non-removably coupled with the proximal end of the instrument 12. In some embodiments, the other extension tube may extend from the proximal end of the instrument 12 to the adapter 36. In some embodiments, the adapter 36 may be integrally formed with the proximal end of the instrument 12. In some embodiments, the adapter 36 may be permanently coupled with the proximal end of the instrument 12 or monolithically formed as a single piece with the proximal end of the instrument 12. In some embodiments, the adapter 36 may be selectively coupled with the proximal end of the instrument 12. For example, the proximal end of the instrument may include a luer fitting 40, as illustrated, for example, in FIG. 2C, which may be coupled with a corresponding luer fitting of the adapter 36. In some embodiments, the luer fitting 40 of the proximal end of the instrument 12 may correspond to and be coupled to a luer fitting of any number of devices. In some embodiments, the proximal end of the instrument 12 may include an instrumentation interface, an electrical connection, and/or an optical connection.

In some embodiments, the proximal end of the instrument 12 may include a curved or angled portion, which may extend through the slot 34 and/or may be coupled to the adapter 36 or another device. In some embodiments, the other extension tube may extend through the slot 34. In some embodiments, the proximal end of the instrument may include an instrument hub, which may facilitate coupling with the adapter. In some embodiments, the instrument hub may include the curved or angled portion and/or may extend through the slot 34. In some embodiments, the instrument hub may be bonded to a distal portion of the instrument 12 via mechanical, adhesive, solvent, ultrasonic, or another suitable type of bonding. For clarity, in some embodiments, the proximal end of the instrument 12 may extend through the slot 34 via either the instrument hub extending through the slot 34 or another portion of the instrument 12 extending through the slot 34.

Figure 2A:
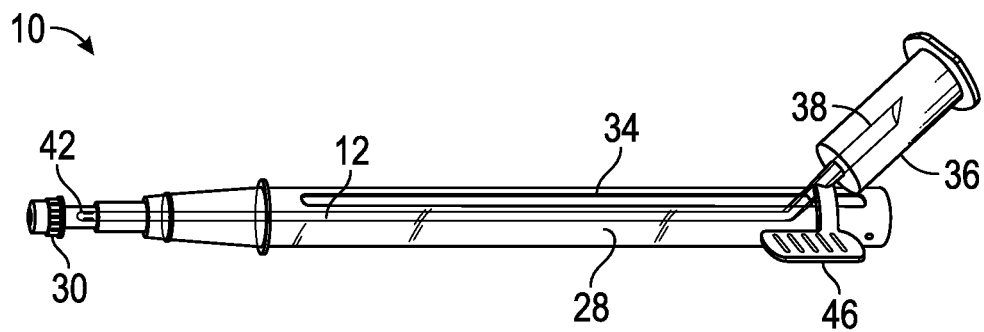
FIG. 2A is an upper perspective view of the extension of FIG. 1A, illustrating an example adapter angled with respect to an example housing, according to some embodiments.
Figure 2B:
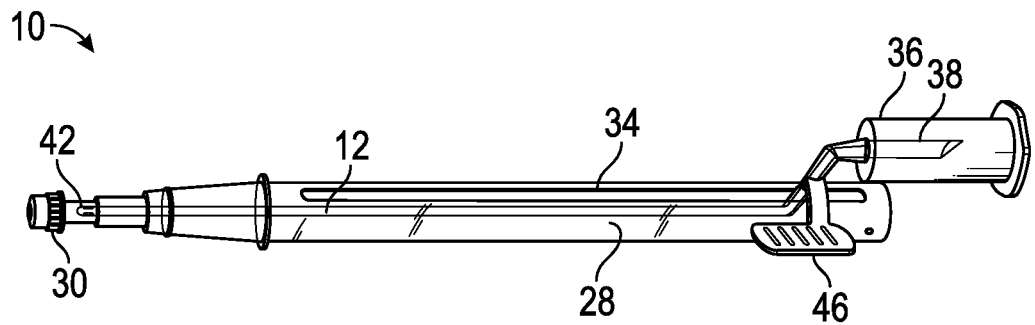
FIG. 2B is an upper perspective view of the another example extension, illustrating the adapter oriented parallel to a longitudinal axis of the housing, according to some embodiments.
Figure 2C:
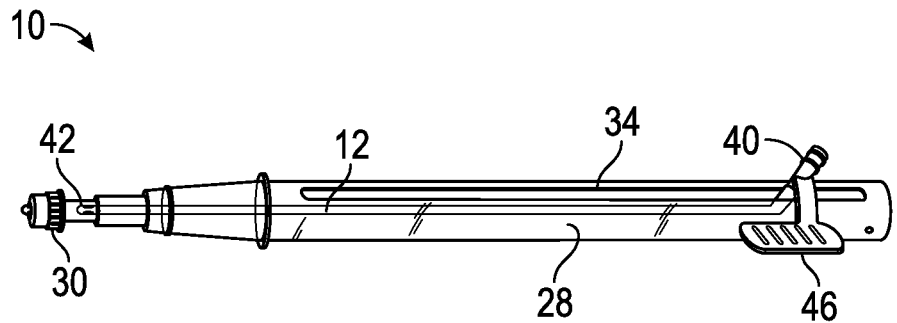
FIG. 2C is an upper perspective view of an example luer fitting disposed at a proximal end of the instrument, according to some embodiments.

In some embodiments, the adapter 36 may be angled with respect to the housing, as illustrated, for example, in FIG. 2A. In some embodiments, the adapter 36 may be oriented parallel to the longitudinal axis of the housing 28, as illustrated, for example, in FIG. 2B.

Figure 2D:
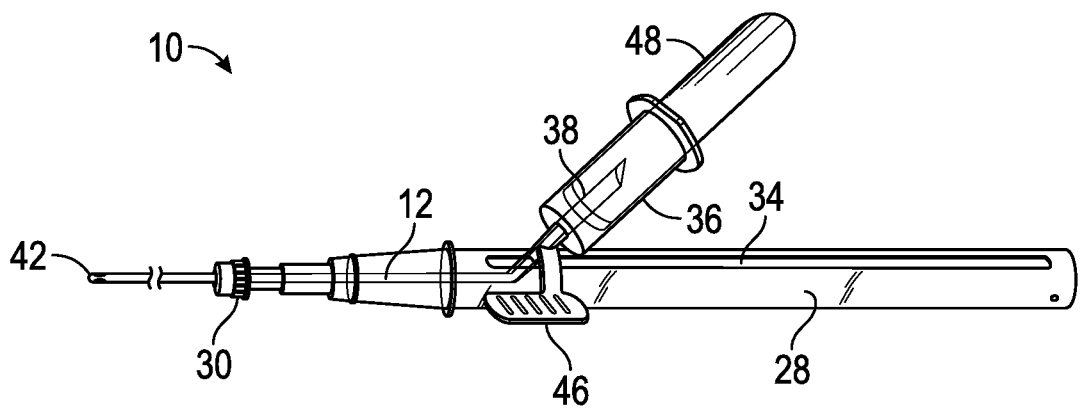
FIG. 2D is an upper perspective view of the extension of FIG. 1A, illustrating an example blood collection tube coupled with the adapter, according to some embodiments.

In some embodiments, the extension may include an advancement tab 46, which may be coupled to the proximal end of the instrument 12 and/or the adapter 36. In some embodiments, the clinician may pinch or grasp the advancement tab 46 to move the instrument 12 to the proximal position and/or the distal position. In some embodiments, the instrument 12 is advanced beyond the distal end of the housing 28 when the adapter 36 is disposed in the distal position. In some embodiments, the advancement tab 36 may be disposed in any number of locations. In some embodiments, the advancement tab 46 may be offset from the slot 34, as illustrated, for example, in FIGS. 2A-2E, which may facilitate easy movement of the instrument 12 and/or the adapter 36 with respect to the slot 34. In some embodiments, the advancement tab 46 may be aligned with the slot 34. In addition or as an alternative to the advancement tab 46, the extension 10 may include one or more other gripping surfaces. For example, the adapter 36 may include one or more gripping surfaces. FIG. 2D illustrates a blood collection tube 48 disposed within the cavity of the adapter 36, according to some embodiments.

Figure 2E:
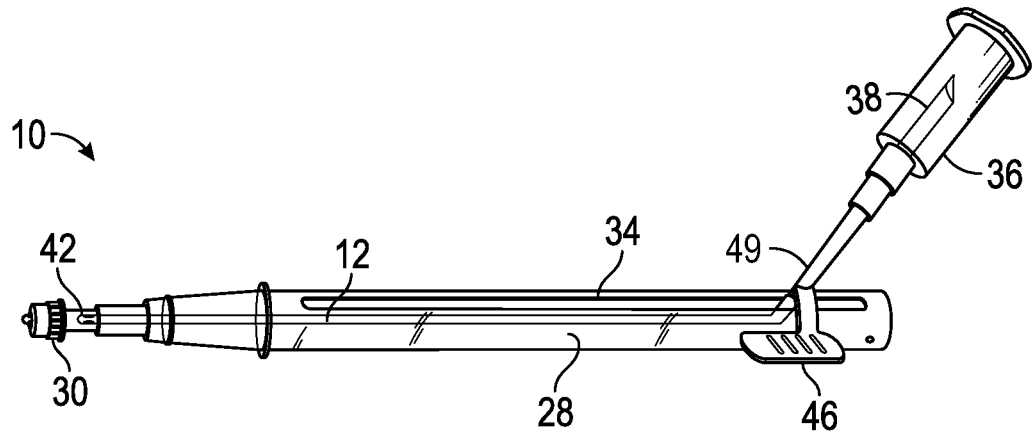
FIG. 2E is an upper perspective view of an example extension tube coupled with the proximal end of the instrument, according to some embodiments.

FIG. 2E illustrates a distal end of an extension tube 49 coupled with the proximal end of the instrument 12, according to some embodiments. In some embodiments, the proximal end of the extension tube 49 may be coupled with the adapter 36 or another device. In some embodiments, the proximal end of the extension tube 49 may include a coupling mechanism, such as, for example, a luer fitting that may be compatible with a luer fitting of the adapter 36 and/or the other device. In some embodiments, the extension tube 49 may be constructed of a flexible material. In some embodiments, the extension tube 49 may facilitate greater compliance and/or flexibility during blood collection, which may reduce disturbance of the catheter 16 and/or the catheter securement dressing.

Figure 2F:
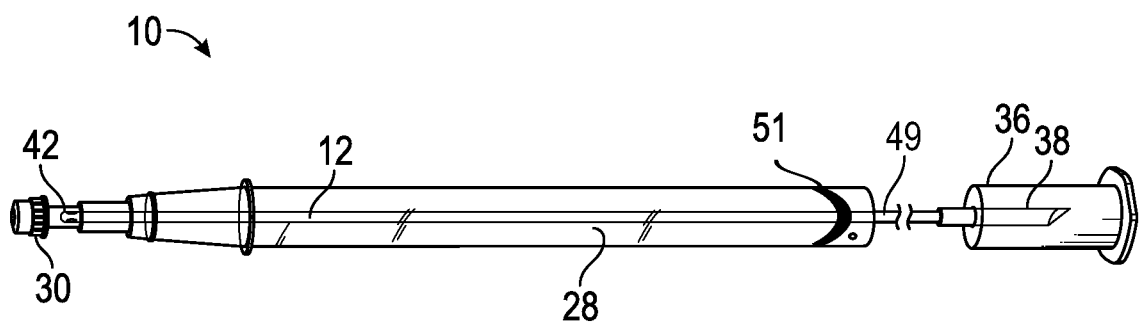
FIG. 2F is an upper perspective view of another example extension tube coupled with the proximal end of the instrument, according to some embodiments.

Referring now to FIG. 2F, in some embodiments, the extension tube 49 may extend through the proximal end of the housing 28. In some embodiments, the extension tube 49 may include an extended length. In these and other embodiments, the housing 28 may not include the slot 34. In some embodiments, the extension tube 49 may be moved distally into the housing 28 to move the instrument to the distal position. In some embodiments, the extension tube 49 may be moved proximally away from the housing to withdraw the instrument to the proximal position. In some embodiments, the extension tube 49 may be rigid or semi-rigid. In some embodiments, the proximal end of the housing 28 may include a barrier 51, which may prevent fluid from leaking out of the proximal end of the housing 28. In some embodiments, the extension tube 49 may extend through the barrier 51.

Figure 2G:
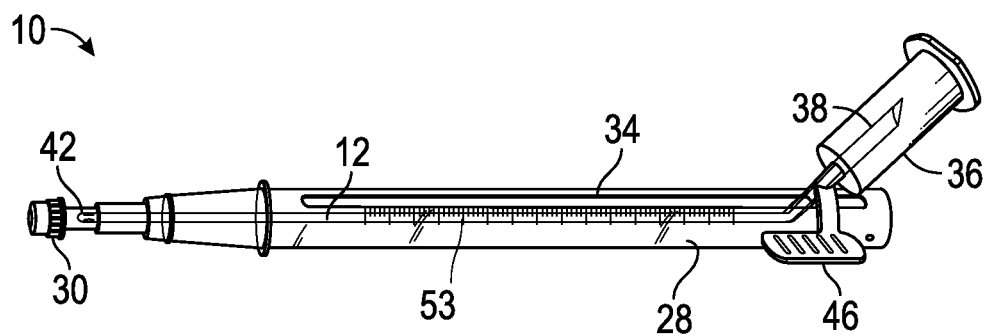
FIG. 2G is an upper perspective view of example markings disposed on an example housing, according to some embodiments.

Referring now to FIG. 2G, in some embodiments, the housing 28 may include one or more markings 53 or measurements, which may visually indicate to the clinician an insertion depth of the instrument 12. In some embodiments, the markings 53 may indicate how far to insert and/or withdraw one or more different instruments 12, which may include different types of catheters, for example. In some embodiments, the extension 10 may include a locking mechanism, which may allow the instrument 12 to be locked in the distal position, the proximal position, or in one or more positions in between the distal and proximal positions. In some embodiments, the instrument 12 may be selectively locked. In some embodiments, the markings may include detents or other features that may permanently or selectively hold the instrument 12. In some embodiments, the markings 53 may indicate one or more of the following: the distal position of the instrument, the proximal position of the instrument, and the positions in between the distal and proximal positions of the instrument.

Figure 2H:
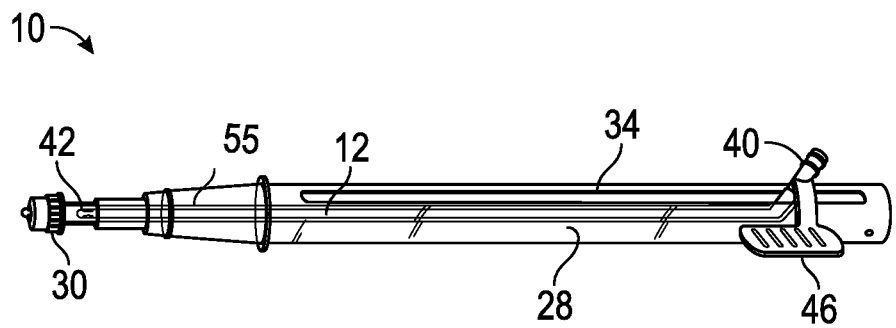
FIG. 2H is an upper perspective view of an example sleeve when the instrument is disposed in the proximal position.
Figure 2I:
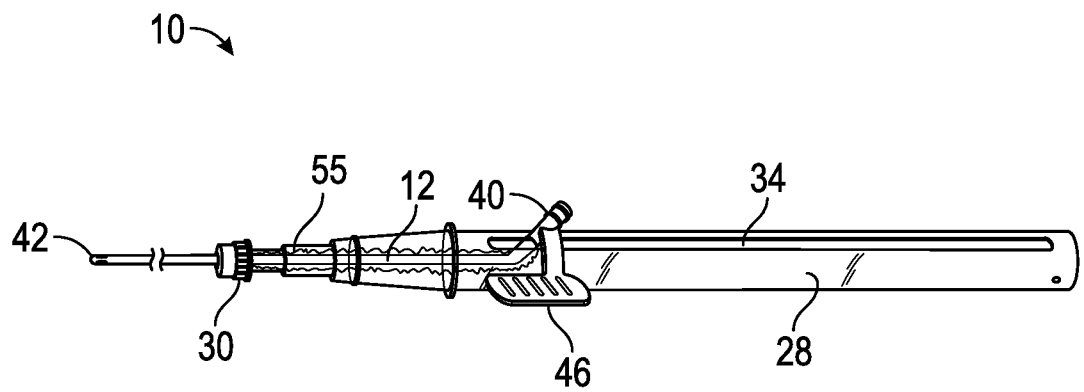
FIG. 2I is an upper perspective view of the sleeve of FIG. 2H when the instrument is disposed in the distal position.

Referring now to FIGS. 2H-2I, in some embodiments, the extension 10 may include the sheath or sleeve 55. In some embodiments, the sleeve 55 may at least partially surround the instrument 12. In these and other embodiments, the sleeve 55 may shield the instrument 12 from contaminants and/or isolate any blood or other fluids that may remain on the instrument 12 after accessing the fluid pathway of the catheter assembly 14. In these and other embodiments, the sleeve 55 may protect the instrument 12 from the external environment surrounding the extension.

In some embodiments, the sleeve 55 may be axially-collapsible or axially-compressible. In further detail, in some embodiments, the instrument 12 may be advanced to the distal position beyond a distal end of the sleeve 55 and/or the catheter 16 when the sleeve 55 is collapsed or compressed in the distal direction, as illustrated, for example, in FIG. 2I. In some embodiments, a proximal end of the sleeve 55 may be coupled with the instrument. For example, a proximal end of the sleeve 55 may be coupled with the proximal end of the instrument 12. In some embodiments, the distal end of the sleeve 55 may be coupled with the coupling mechanism 30 or another portion of the housing 28. In some embodiments, the sleeve 55 may or may not extend through the slot 34.

Figure 3:
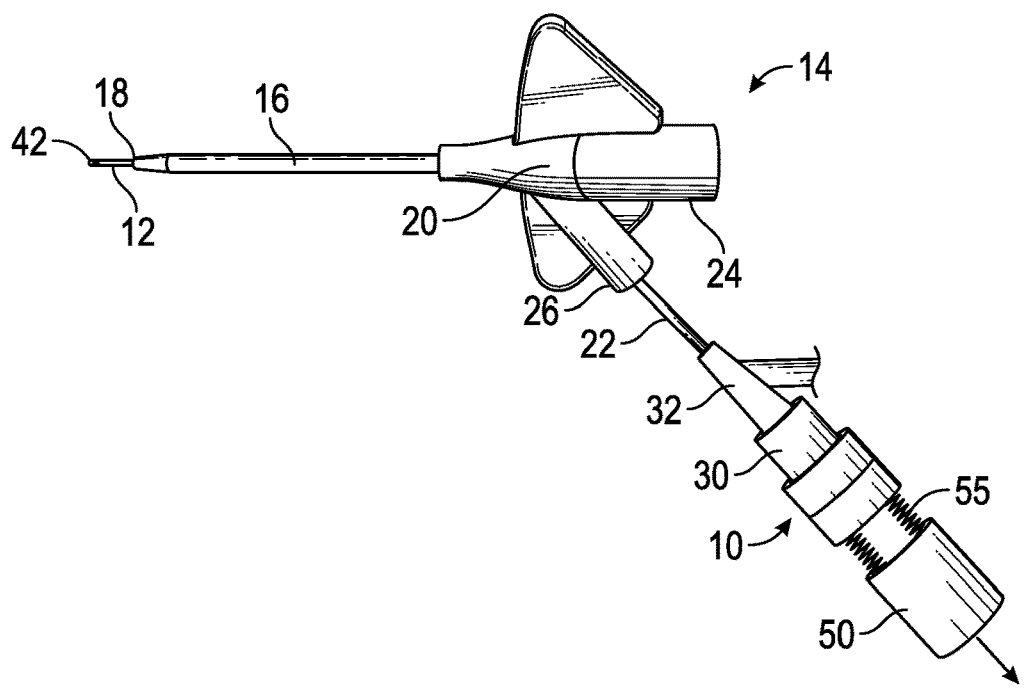
FIG. 3 is an upper perspective view of another catheter system, illustrating another example housing, according to some embodiments.

Referring now to FIG. 3, in some embodiments, at least a portion of the sleeve 55 may be axially-compressible or axially-collapsible. In further detail, in some embodiments, the instrument 12 may be advanced to a position beyond the distal end of the sleeve 55 when the sleeve 55 is compressed or collapsed in the distal direction. In some embodiments, the extension 10 may include a hub or grip 50, which may be coupled to a proximal end of the sleeve 55. In some embodiments, a clinician may move the grip 50 distally to compress or collapse the sleeve 55 in the distal direction and advance the instrument 12 to the position beyond the distal end of the sleeve 55. In some embodiments, a clinician may move the grip 50 proximally to expand the sleeve 55 in a proximal direction and withdraw the instrument 12 into the sleeve 55, wherein the instrument 12 may be locked. In some embodiments, the grip 50 and/or the instrument 12 may be coupled with, for example, the adapter 36, another device, an instrumentation interface, an electrical connection, and/or an optical connection. In some embodiments, as illustrated in FIG. 3, the extension 10 may not include the housing 28.

Figure 4:
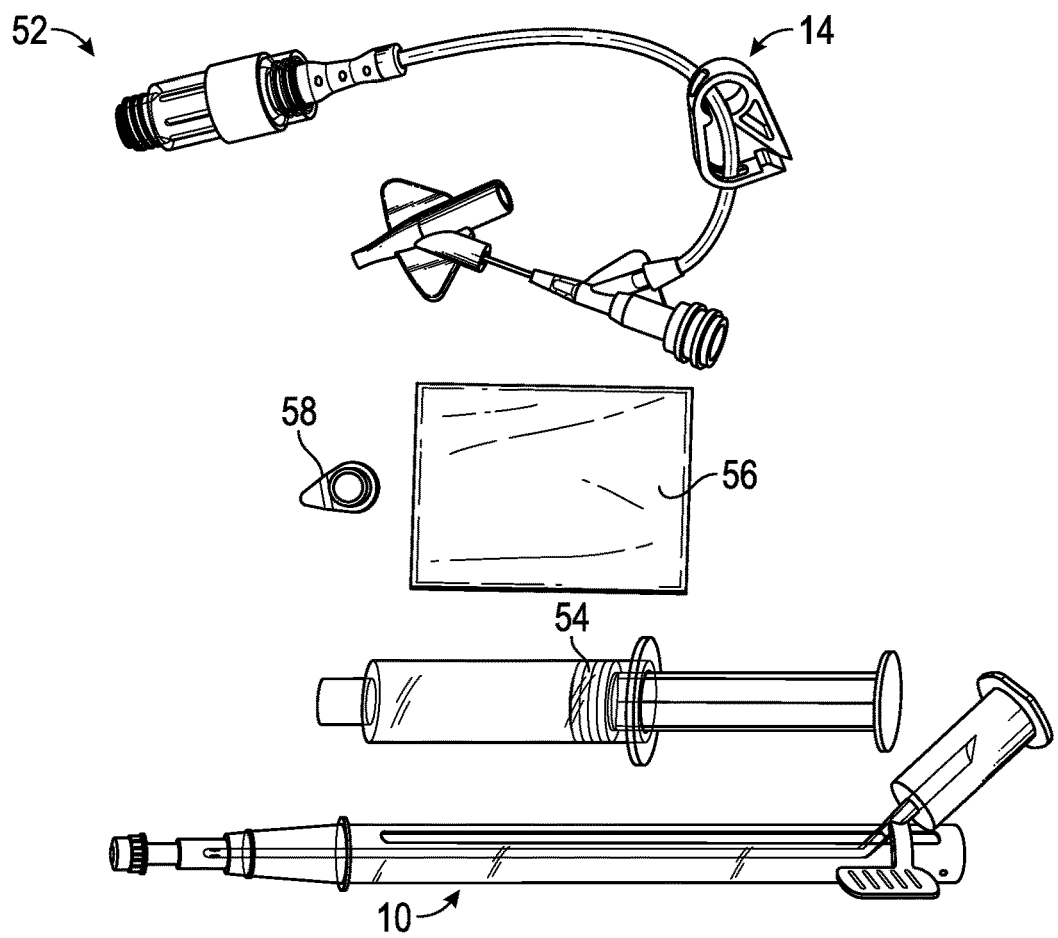
FIG. 4 is an upper perspective view of an example kit, according to some embodiments.

Referring now to FIG. 4, in some embodiments, a kit 52 may include one or more of the following: the catheter assembly 14, the extension 10, the syringe 54, the blood collection tube 48, an alcohol swab 56, one or more disinfection caps 58, and catheter securement dressing (not illustrated). In some embodiments, the dressing may include an extension tube slot and/or one or more antimicrobial agents. In some embodiments, the disinfection caps 58 may include one or more antimicrobial agents and/or may be configured to close the coupler element 32 and/or one or more catheter adapter ports. Specifically, in some embodiments, the kit 52 may include a blood collection or line draw kit, and the instrument 12 may include the other catheter.

In some embodiments, a method of using the extension 10 and/or the kit 52 may include disinfecting the coupler element 32 with the alcohol swab 56. In some embodiments, following the disinfecting of the coupler element 32, the extension 10 may be coupled with the catheter assembly 14 via the coupler element 32. In some embodiments, the catheter assembly 14 may have been previously inserted into the vasculature of the patient. In some embodiments, the instrument 12 may then be advanced through the fluid pathway of the catheter assembly 14 and/or the distal tip 42 of the instrument may be placed into the vasculature distal to the tip 18 of the catheter 16. In some embodiments, following the advancement of the instrument, the syringe 54, which may be pre-filled, may be used to flush the catheter assembly 14 to remove stagnant blood and/or medication. In some embodiments, a plunger of the syringe 54 may be pulled to withdraw a discard sample. In some embodiments, the blood collection tube 48 may be coupled with the adapter 36 to obtain a blood sample. In some embodiments, following blood collection and/or probing, the extension 10 may be uncoupled from the catheter assembly 14 and the disinfection cap 58, which may include one or more antimicrobial agents, may be placed on the coupler element 32 for disinfection. In some embodiments, one or more steps of the method may be optional, such as, for example, flushing the catheter assembly 14 and/or withdrawing the discard sample. In some embodiments, the extension 10 may be discarded after use.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A vascular access device, comprising:
a catheter assembly comprising a catheter adapter having a distal end from which a catheter extends, a first port formed at a proximal end by which an introducer needle having a sharp distal tip for puncturing and configured to introduce the catheter into vasculature is selectively coupled to the catheter adapter, a lumen extending between the distal end and the proximal end of the catheter adapter, and a side port positioned between the distal end and the proximal end of the catheter adapter; and
an extension comprising:
a housing having a proximal end, a distal end having a luer fitting that is coupled to the side port of the catheter adapter, and a slot, wherein the slot comprises a proximal end and a distal end, wherein the proximal end of the slot is distal to the proximal end of the housing; and
another catheter disposed within the housing, wherein the another catheter comprises a proximal end and a distal portion forming a blunt distal tip through which blood can be collected, wherein the proximal end of the another catheter extends out through the slot to form a blood collection adapter, the proximal end of the another catheter, including the blood collection adapter, being configured to move along the slot from a proximal position distal to the proximal end of the slot to a distal position, wherein the vascular access device is configured such that, when the proximal end of the another catheter is in the proximal position distal to the proximal end of the slot, the blunt distal tip of the another catheter is disposed within the housing, wherein in response to movement of the proximal end of the another catheter from the proximal position to the distal position and withdrawal of the introducer needle, the blunt distal tip of the another catheter is configured to advance out through the catheter to thereby enable blood to be collected directly from a patient's vasculature via the blood collection adapter, and wherein the lumen is aligned with the first port when the another catheter is in the distal position.

2. The vascular access device of claim 1, wherein the blood collection adapter comprises a cavity configured to receive a syringe or a blood collection tube, wherein the blood collection adapter further comprises a cannula disposed within the cavity and configured to puncture a septum of the syringe or the blood collection tube in response to the syringe or the blood collection tube being advanced into the cavity of the blood collection adapter.

3. The vascular access device of claim 2, wherein the blood collection adapter is angled with respect to the housing.

4. The vascular access device of claim 1, wherein the housing is rigid or semi-rigid.

5. The vascular access device of claim 1, wherein the blood collection adapter is oriented parallel to a longitudinal axis of the housing.

6. The vascular access device of claim 1, further comprising an advancement tab coupled with the another catheter.

7. The vascular access device of claim 6, wherein the advancement tab is offset from the slot.

8. The vascular access device of claim 1, wherein the catheter assembly further includes a Y adapter that is coupled to the side port, the distal end of the housing being coupled to the side port via a first port of the Y adapter.

9. The vascular access device of claim 1, wherein the blunt distal tip of the another catheter includes a plurality of holes.

10. The vascular access device of claim 1, wherein the catheter assembly further includes a valve that forms a fluid seal between the side port and the housing, and wherein the blunt distal tip of the another catheter is configured to penetrate the valve.

11. The vascular access device of claim 1, wherein the distal portion of the another catheter has a smaller outer diameter than a proximal portion of the another catheter.

12. The vascular access device of claim 1, wherein a stiffness of the another catheter varies along a length of the another catheter.

13. The vascular access device of claim 12, wherein the distal portion of the another catheter is less rigid than a proximal portion of the another catheter.

14. The vascular access device of claim 1, wherein the catheter assembly includes a septum disposed within the lumen of the catheter adapter.

15. The vascular access device of claim 1, wherein the proximal end of the another catheter that extends out through the slot comprises an extension tube.

16. The vascular access device of claim 1, further comprising:
a syringe that is configured to couple to the blood collection adapter.

17. The vascular access device of claim 1, further comprising:
a blood collection tube that is configured to couple to the blood collection adapter.

18. The vascular access device of claim 1, wherein the luer fitting is configured to be spaced apart from the introducer needle when the introducer needle is inserted through the catheter adapter.

* * * * *